(12) United States Patent
Dardenne et al.

(10) Patent No.: US 10,092,305 B2
(45) Date of Patent: Oct. 9, 2018

(54) SYSTEM AND METHOD OF NAVIGATION-GUIDED OSTEOTOMY

(71) Applicant: OSTESYS, Plouzane (FR)

(72) Inventors: Guillaume Dardenne, Montreuil le Gast (FR); Pierre-Yves Huet, Locmaria-Plouzane (FR); Stephane Lavallee, St. Martin d'Uriage (FR); Christian Lefevre, Brest (FR); Eric Stindel, Locmaria-Plouzane (FR); Romain Gerard, Brest (FR)

(73) Assignee: OSTESYS, Plouzane (FR)

( * ) Notice: Subject to any disclaimer, the term of this patent is extended or adjusted under 35 U.S.C. 154(b) by 521 days.

(21) Appl. No.: 14/416,465

(22) PCT Filed: Jul. 26, 2013

(86) PCT No.: PCT/EP2013/065777
§ 371 (c)(1),
(2) Date: Jan. 22, 2015

(87) PCT Pub. No.: WO2014/016399
PCT Pub. Date: Jan. 30, 2014

(65) Prior Publication Data
US 2015/0182236 A1    Jul. 2, 2015

Related U.S. Application Data

(60) Provisional application No. 61/676,376, filed on Jul. 27, 2012.

(30) Foreign Application Priority Data

Sep. 6, 2012  (FR) ...................................... 12 58319

(51) Int. Cl.
*A61B 17/88* (2006.01)
*A61B 17/17* (2006.01)
(Continued)

(52) U.S. Cl.
CPC .......... *A61B 17/1728* (2013.01); *A61B 17/17* (2013.01); *A61B 17/1703* (2013.01);
(Continued)

(58) Field of Classification Search
None
See application file for complete search history.

(56) References Cited

U.S. PATENT DOCUMENTS

2010/0160917 A1* 6/2010 Fitz ...................... A61B 5/4528
606/88
2011/0196377 A1* 8/2011 Hodorek .............. A61B 17/155
606/87

FOREIGN PATENT DOCUMENTS

DE      102007008521 A1    8/2007
FR          2941362 A1    7/2010
(Continued)

OTHER PUBLICATIONS

International Search Report from corresponding PCT/EP2013/065777, dated Oct. 25, 2013.
(Continued)

*Primary Examiner* — Sameh Boles
(74) *Attorney, Agent, or Firm* — Womble Bond Dickinson (US) LLP

(57) ABSTRACT

The invention relates in particular to a system for attaching a first bone segment to a second bone segment, the two segments belonging to the same bone, in which the first and second segments are held together via a hinge resulting from the partial transverse cutting of said bone, characterized by the fact that said system comprises:
  two targets suitable for attaching to the two segments of said bone;
  a navigation system suitable for acquiring the three-dimensional positions and orientations of the targets;
    —a processing system suitable for calculating, based
(Continued)

Figure 1:
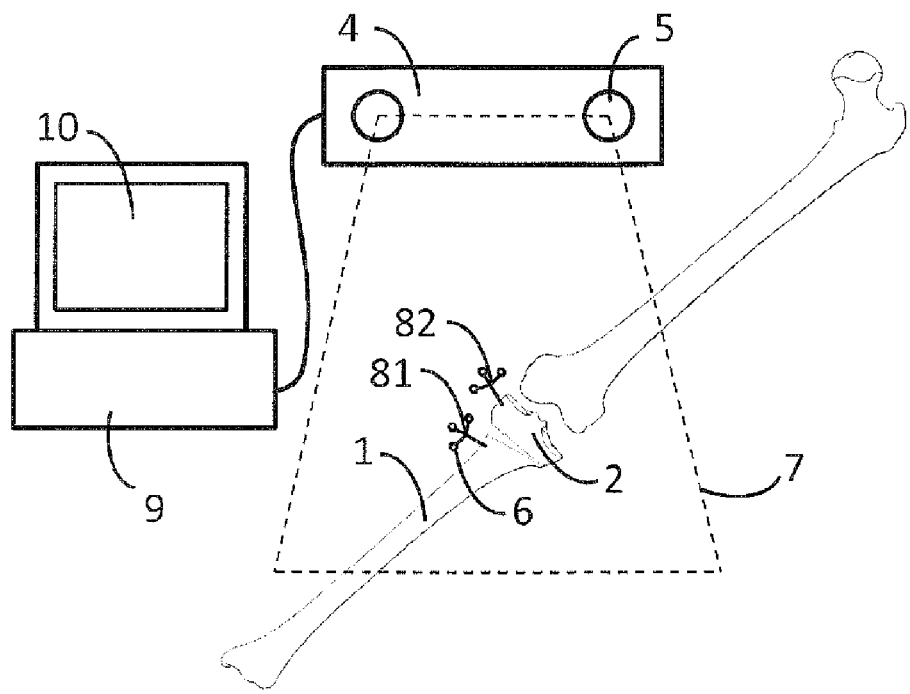

on the data sent from the navigation system, the angles corresponding to the three-dimensional alignment of said two segments;
a display unit suitable for displaying the information to the surgeon; at least one milling guide;
a plurality of implants of different sizes.

17 Claims, 7 Drawing Sheets

(51) Int. Cl.
*A61B 17/80* (2006.01)
*A61B 34/00* (2016.01)
*A61B 17/56* (2006.01)
*A61B 90/00* (2016.01)
*A61B 34/20* (2016.01)

(52) U.S. Cl.
CPC ...... *A61B 17/1707* (2013.01); *A61B 17/8009* (2013.01); *A61B 17/8023* (2013.01); *A61B 17/8095* (2013.01); *A61B 17/8866* (2013.01); *A61B 34/20* (2016.02); *A61B 34/25* (2016.02); *A61B 2017/565* (2013.01); *A61B 2034/2055* (2016.02); *A61B 2090/3983* (2016.02)

(56) References Cited

FOREIGN PATENT DOCUMENTS

| WO | 0237935 A2 | 5/2002 |
| WO | 2008039269 A2 | 4/2008 |
| WO | 2011055353 A1 | 5/2011 |

OTHER PUBLICATIONS

Yamamoto, "Validation of Computer-assisted Open-wedge High Tibial Osteotomy Using Three-dimensional Navigation", Orthopedics, Slack, US, vol. 31, No. 10, Suppl. 1, Oct. 1, 2008, pp. 68-71, XP009169494.

BrainlabCorporate, "Dash—Computer Assisted Joint Replacement with the ipod touch", Feb. 17, 2001, p. 1, XP054975144.

* cited by examiner

SYSTEM AND METHOD OF NAVIGATION-GUIDED OSTEOTOMY

CROSS REFERENCE TO RELATED APPLICATIONS

This application is a § 371 National Stage Application of PCT/EP2013/065777, filed Jul. 26, 2013, which claims priority to U.S. 61/676,376, filed Jul. 27, 2012, and FR 1258319, filed Sep. 6, 2012.

BACKGROUND

Field of the Invention

Osteoarthritis is a mechanical abnormality involving degradation of the joints, including articular cartilage and subchondral bone.

Description of Related Art

This pathology can be treated using different methods. The most common one is the total replacement of the diseased joint with a prosthetic implant. This method is however very degenerative, invasive and sometimes traumatic for the patient.

When this disease is the consequence of a misalignment of a limb, it can be delayed or treated with an osteotomy. This surgical procedure, less invasive, aims to rebalance the stress on the diseased joint by realigning the joint centers of the limb (for instance hip, knee and ankle centers for the lower limb and shoulder, elbow and wrist for the upper limb). A partial cut is performed on one of the two bones forming the limb (for instance femur or tibia for the lower limb, and, humerus or radius for the upper limb).

The realignment is made by rotating the two cut bony segments, partially cut, around a rotation point called hinge resulting from the partial cut. Once the alignment has been reached, the two cut bony segments are maintained in the wanted position, in most cases, with an osteosynthesis plate positioned above the cutting and resting on the two segments.

However, despite the good results of this procedure, osteosynthesis plates must be usually removed with a second surgery because of an additional thickness onto the bone which can lead to overlying soft tissue irritations and discomfort for the patient.

The system called "IBALANCE" commercialized by the company ARTHREX provides a technique allowing the surgeon to insert and fix with screws a wedge implant inside the opening, due to the distraction of the two bony segments. This implant maintains the relative positions of the two bony segments and avoids the over-thickness of conventional osteotomy plates. The aim of this implant is to avoid soft tissue irritations and therefore the second surgery.

The IBALANCE solution has however several drawbacks:

The resulting alignment can be inaccurate and can lead to bad post-operative results since the required correction angle to align the lower limb is planned preoperatively in simple two-dimensions (2D) radiographies and is reported during the surgery with a simple geometric ruler;

The solution cannot adjust the alignment of the limb in the three required rotations of the space. Only the rotation in the frontal plane can be realized, the slope (rotation in the sagittal plane) and the coronal rotations cannot be correctly adjusted which can lead also to non-optimal postoperative results

SUMMARY

It is an object of the present invention to provide a system for the placement of a wedge implant for osteotomies inside the opening allowing the surgeon to adjust and maintain with a high accuracy the alignment of the two bony segments in the three dimensions (3D).

In this regard, the invention is a system for attaching a first bony segment in relation with a second bony segment.

This system of attachment of a first bony segment in relation with a second bony segment, both segments belonging to a same bone, wherein the first and second segments are maintained together with a hinge coming from the partial cut of the said bone, characterized in that the system comprises:

Two trackers adapted to be attached to both segments of said bone,
A navigation system adapted to acquire the three-dimensional positions and orientations of said trackers,
A processing system adapted to compute, from the data given by said navigation system, the three dimensional alignment angles of the two said segments,
A display unit adapted to show information to the surgeon,
At least one reaming guide,
Several implants of different size;

DETAILED DESCRIPTION OF A PREFERRED EMBODIMENT

According to other non-limiting and advantageous features of the invention, individually or in combination:
each tracker is attached to a base fixed with at least one pin or screw to each said segment;
each base is composed of two fixing pins and a receiving support of the corresponding tracker;
it comprises at least one spacer used to maintain the desired position between both segments;
the said at least one spacer is attached between both bases;
the said at least one spacer is adjustable in length;
the said reaming guide is adjustable, especially in length, so as to be adapted according to the distraction of the bone segments;
the said reaming guide has at least one reaming hole with a specific shape;
the said reaming guide comprises at least one fixation system in relation with the bone;
the said reaming guide is attached onto said base;
the said fixation system permits to detach said reaming guide and to replace it by another one;
the said fixation system is a locked tenon and mortise joint;
the said implant has the same volume as the distraction size and the said reamed global volume;
the said implant is adjustable following the said distraction size;
the said display unit and/or the said processing system is directly carried by at least one of the said trackers;
the trackers are optic or magnetic.

The distraction between both segments is performed in 3D in order to adjust the frontal rotation in the frontal plane, the sagittal rotation in the sagittal plane and the coronal rotation in the coronal plane. Knowing the 3D positions and orientations of the trackers, the processing system can automatically compute in real time during the distraction the alignment angles. A specific display unit allows the surgeon to visualize the alignment information.

Once the desired alignment has been reached, the positions of both bony segments can be maintained if necessary with spacers. A reaming guide is then placed whatever the 3D alignment in front of the opening of the bone in order to ream a volume of bone on the first bony segment and a volume of bone on the second bony segment. This reaming guide could be directly adjustable in length or there could be different models of reaming guide with different size in order to ream both volumes of bone whatever the size of the distraction. In the case of different models, the processing system could automatically compute the size of the reaming guide model to use, according to the distraction. The reaming can be then performed by following the reaming hole of the guide with a reamer.

Once the reaming has been performed, the wedge implant can be placed. Several wedge implant models of different size can be available in order to fit correctly the reamed volume whatever the distraction. The implant model, which must be placed, could be given automatically by the processing system to the user following the size of the distraction. In order to have a well-fitting, the geometry of the wedge must be the same as the reamed volume with the distraction. The implant can be finally fixed in order to maintain both bony segments in the desired 3D alignment with at least one screw per segment.

Thus, a second aspect of the invention relates to a method of attachment of a first bony segment in relation with a second bony segment, both segments belonging to a same bone, wherein the first and second segments are maintained together with a hinge coming from a transverse partial cut of the said bone, and wherein a tracker has been attached beforehand to each of the two said segments, method characterized by comprising the following steps:

distracting the said first segment with respect to the said second segment of the said bone around said hinge until reaching the desired three dimensional alignment;
visualizing the three dimensional alignment between both said segments;
maintaining the two segments in the desired three dimensional alignment;
placing a reaming guide facing the two segments;
reaming a first volume of bone of the first segment and a second volume of bone of the second segment;
choosing one good implant size in relation with the distraction size and the global volume comprising the said first and the second volumes;
placing the implant chosen inside the said global volume;
maintaining the said implant between the said first and second segments.

The invention and its advantages will be described in more details below with references to the accompanying schematic drawings, which for the purpose of illustration show some non-limiting embodiments, and in which:

The FIG. 1 is a schematic representation of the required hardware for the determination of the 3D alignment of the bony segments.

Figure 2:
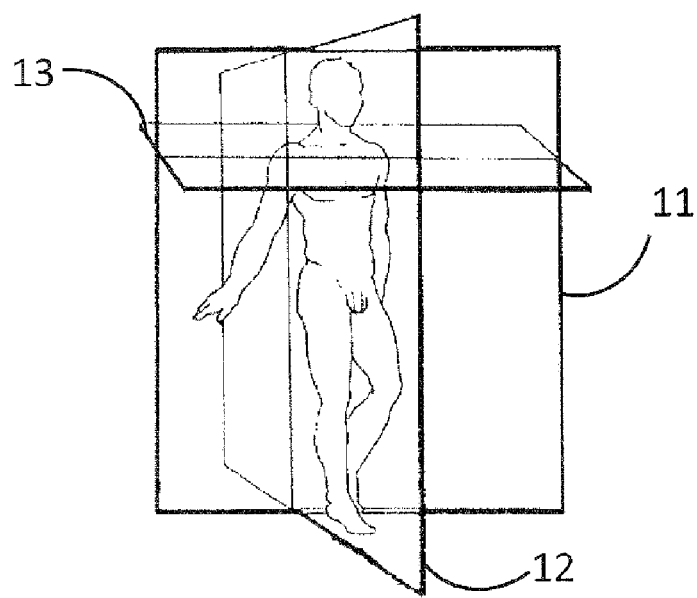

The FIG. 2 is a schematic representation of the anatomical reference system.

Figure 3:
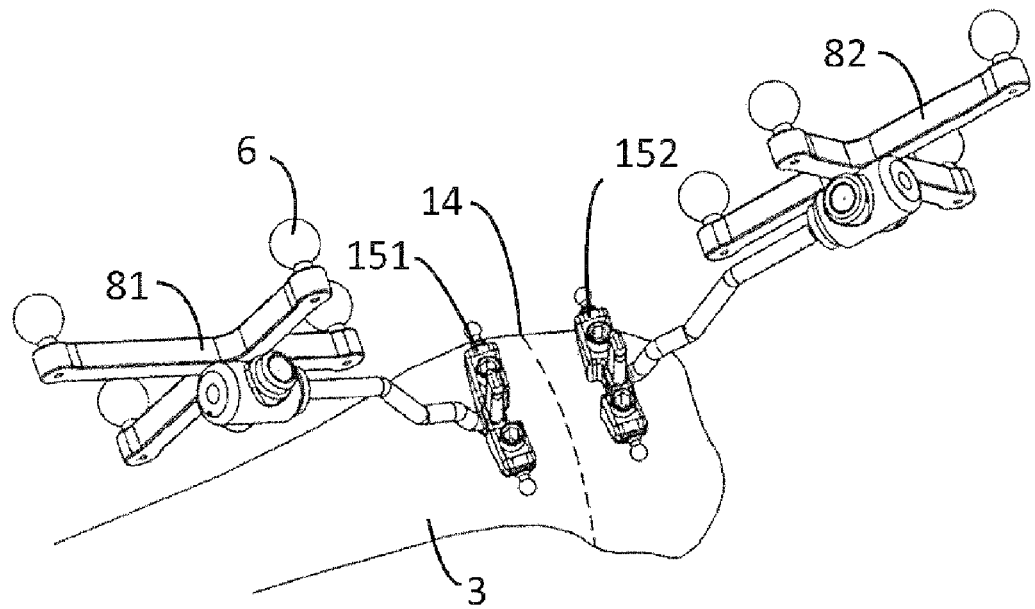

The FIG. 3 is a schematic drawing of the bone with the two trackers before the osteotomy.

Figure 4:
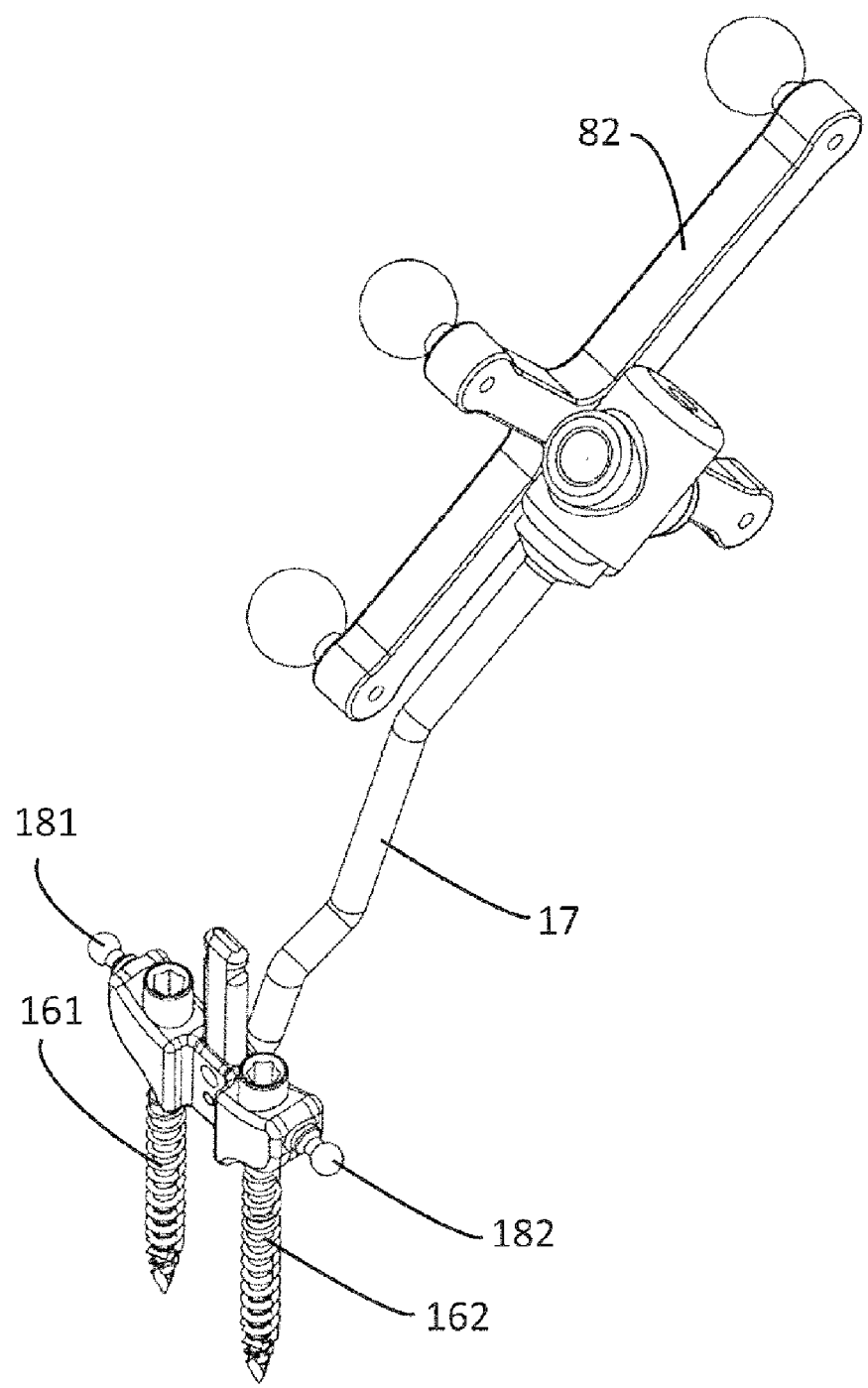

The FIG. 4 is a schematic drawing of the fixation mean of the trackers to the bone.

Figure 5:
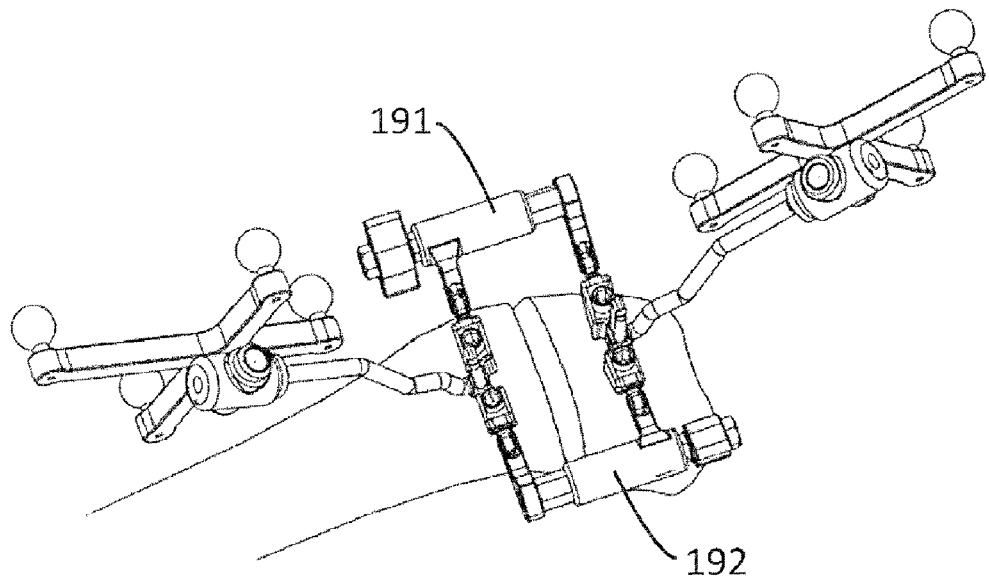

The FIG. 5 is a schematic drawing of the distraction process in 3D with spacers.

Figure 6:
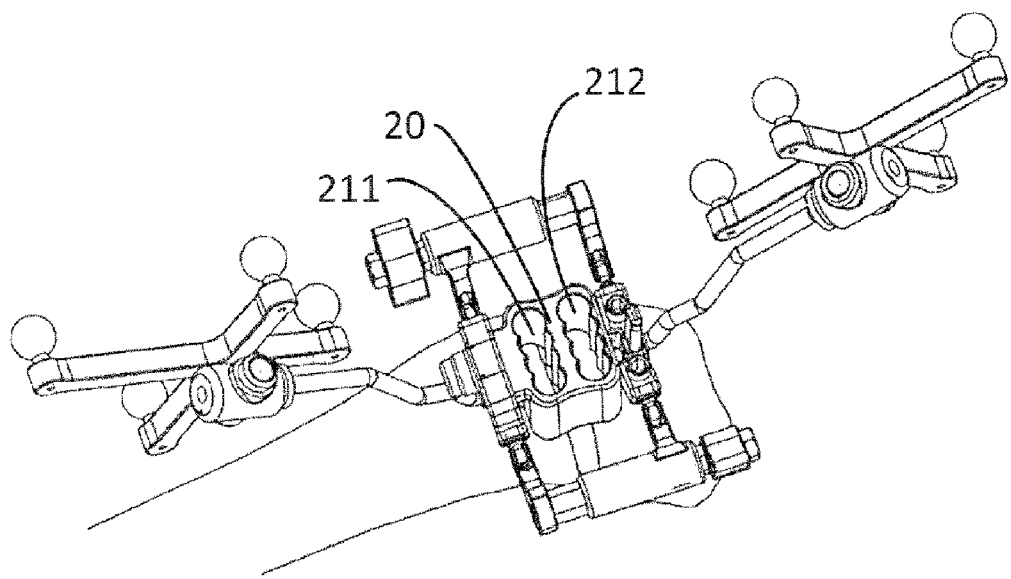

The FIG. 6 is a schematic drawing of the placement of the reaming guide.

Figure 7:
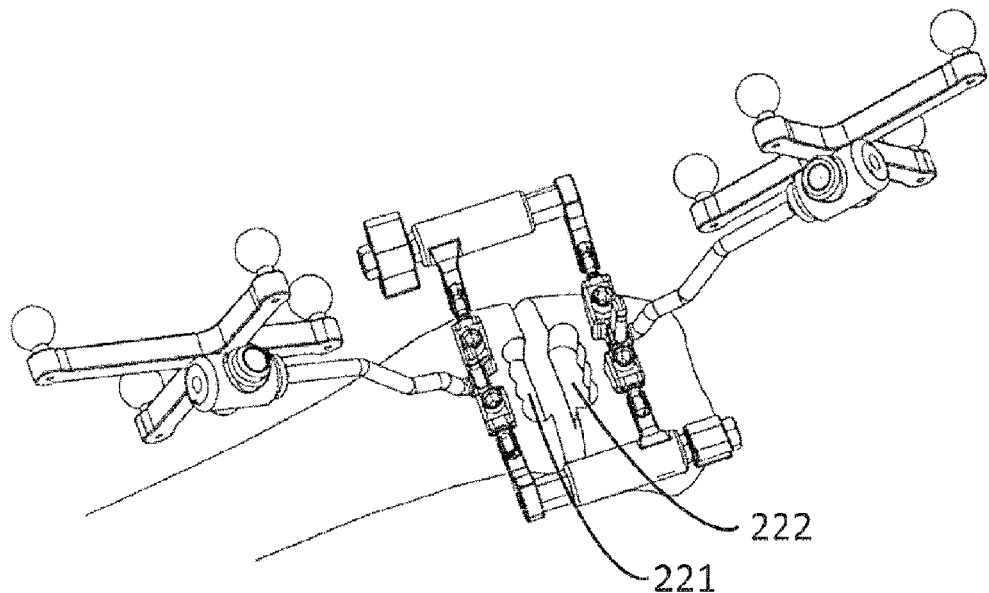

The FIG. 7 is a schematic drawing of the reamed volume of the bone.

Figure 8:
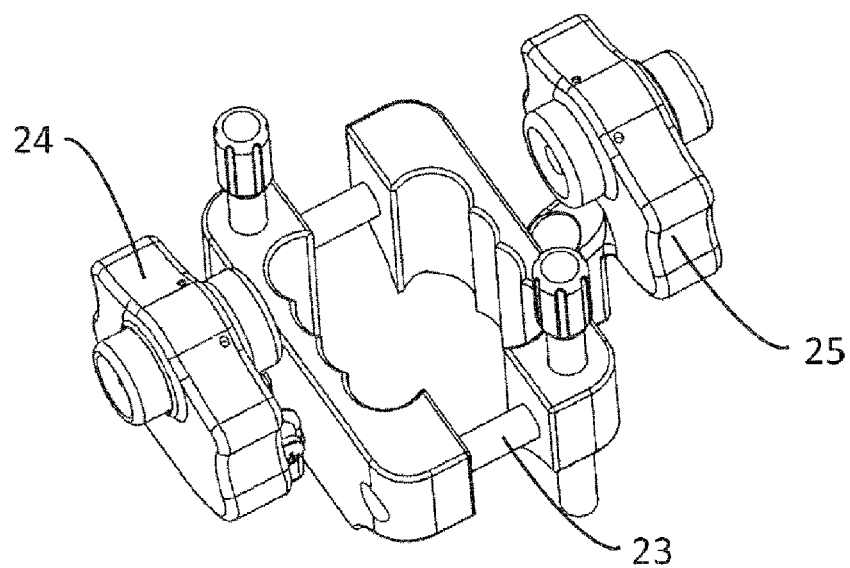

The FIG. 8 is a schematic drawing of an adjustable reaming guide.

Figure 9:
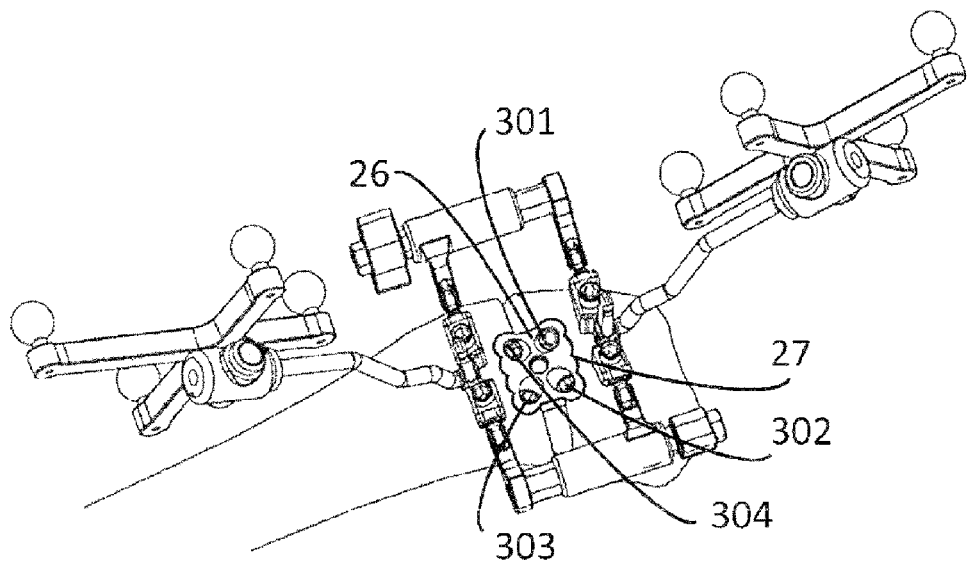

The FIG. 9 is a schematic drawing of the placement of the implant.

Figure 10:
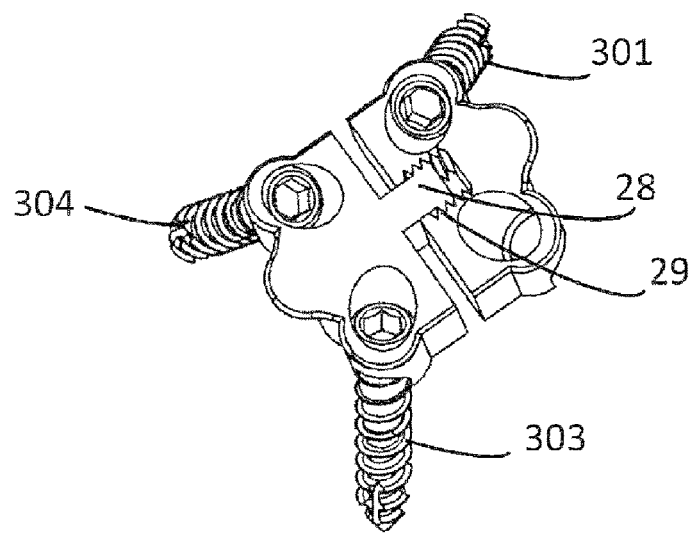

The FIG. 10 is a schematic drawing of an adjustable implant.

Figure 11:
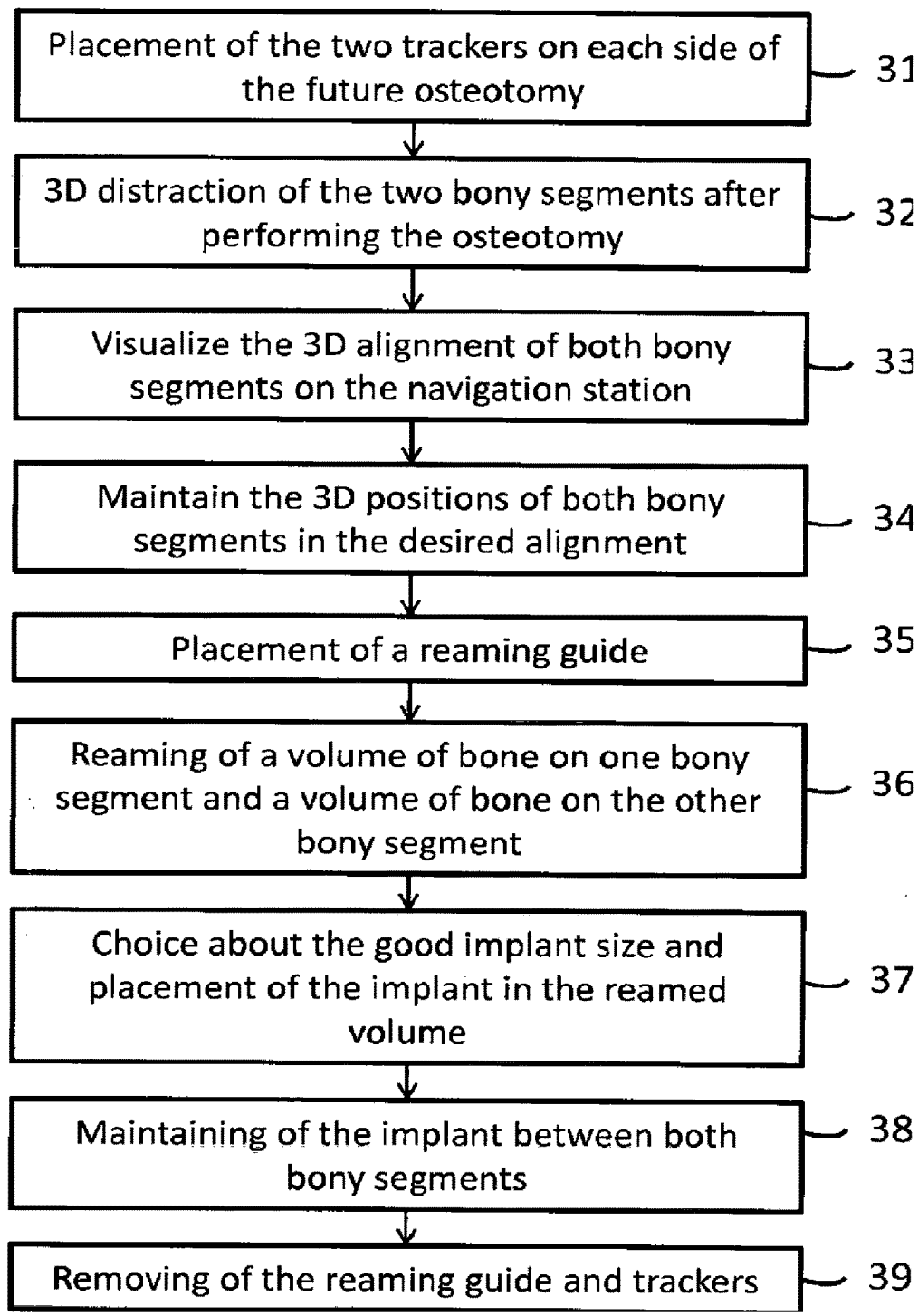

The FIG. 11 is the surgical procedure flow diagram.

The following detailed description refers primarily to the open wedge tibia osteotomy as an example. However, the present invention can also be used with other type of osteotomies.

FIG. 1 shows the required hardware for determining the 3D alignment of a first bony segment 1 with respect to a second bony segment 2 composing the bone 3 (FIG. 3). This hardware is composed of a 3D localizer 4 equipped with cameras 5 which can determine by triangulation the 3D positions of markers 6 in the space 7 visible by the localizer. Two trackers 81 and 82 of a known type, containing at least three markers 6 and allowing the processing device 9 connected to the localizer 4 to compute their 3D positions and orientations, are fixed on the first and the second bony segments. The trackers 81 and 82 and the localizer 4 may be any commercially available system, such as, for instance, that marketed by the company NORTHERN DIGITAL under the trademark POLARIS. The screen 10 can provide 3D alignment information to the surgeon including for instance the frontal rotation in the frontal plane 11, the sagittal rotation in the sagittal plane 12 and the coronal rotation in the coronal plane 13 in the FIG. 2.

For this instance, the system is an optical localizing device; however, all other localizing device like magnetic, ultrasound, accelerometer, etc. could be used under this innovation.

FIG. 3 shows both trackers 81 and 82 fixed onto the two segments of the bone 3 on each side of the future cut 14 via two bases: the base 151 for the tracker 81 and the base 152 identical to the previous for the tracker 82. As part of this invention, these trackers can be attached to the bone by any other mean of fixation.

FIG. 4 shows a base which is composed of two pins 161 and 162 which are used to fix the base onto the bone, and a tracker support 17 allowing the base to receive the corresponding tracker, for instance the tracker 82. Two ball-joints 181 and 182 are also available in order to attach spacers for "distracting" (i.e move apart) and/or maintaining the distraction of both bony segments.

These spacers 191 and 192, visible in the FIG. 5 can support effort of the distraction and are adjustable in length. The ball joint fixation system between the spacers and the bases allows the user to adjust the distraction in 3D. The 3D alignment is known by the user thanks to the screen 10 of the navigation station. Knowing the 3D positions and orientations of the two trackers in the space with the camera 4, the processing device computes the 3D alignment in real time during the distraction process. As part of this invention, the distraction can be performed manually or by any other mean of spacer.

FIG. 6 shows the placement of a reaming guide 20 facing the two bony segments. Two reaming shapes 211 and 212 allow the user to ream a volume of bone 221 of the segment 1 and a volume of bone 222 of the segment 2 as shown in the FIG. 7. In this instance, the reaming guide is directly maintained with a specific fixation system to bases which support the tracker to avoid having to use additional pins or screws to the bone. All other fixation system for the reaming guide is also in the scope of this invention.

In this instance, several size of reaming guide is available following the distraction size.

The good guide size to use can be obtained directly with the navigation station which can compute automatically the required reaming guide model given the distraction size.

An adjustable reaming guide which can be adapted whatever the distraction could be also used under this invention, as shown in FIG. 8. In this case, this reaming guide is composed of a spreadable part 23 which can automatically be adjusted following the distraction value. Two fixation systems 24 and 25 can maintain the adjustable reaming guide between both segments via, for instance, the two bases 151 and 152 in order to avoid the use of additional pins or screws in the bone. Again, all other fixation system could be used under this invention.

All other mean of reaming allowing the user to ream both volumes of bone on both bony segments whatever the 3D distraction can be used under this invention.

Once the reaming has been performed, the implant 26 of the FIG. 9 can be placed in the global volume composed of the first volume 221, the second volume 222 and the distraction length as shown in the FIG. 7. The shape of the implant 27 in the FIG. 9 must be the same as this global volume in order to have a good fitting and a good stability between the bone and the implant, and thus, to avoid modification of the 3D alignment after fixation. All other reaming guide having other shape for the reaming hole with the corresponding implants having the same shape can be used under this invention. In this instance, several sizes of implant are available following the distraction size and the reamed volume. The good size of the implant can be obtained directly with the navigation station which can compute automatically the required implant size given the distraction. An adjustable implant which can be adapted in length whatever the distraction could be also used under this invention. As shown in the FIG. 10, an adjustable part 28 allows the implant to be adjustable in length. This adjustable part is composed of teeth 29 which can support high compressive forces. The implant is then maintained inside the global volume with screws 301, 302, 303 and 304 between both segments in order to have a well attachment. All other fixation means can be used under this invention.

The FIG. 11 shows the overall surgical procedure with successive specific and innovative steps for the attachment of a first bony segment in relation with a second bony segment. The surgeon must first attach two trackers in both sides of the future osteotomy (step 31). After performing the osteotomy, the surgeon can accurately distract both bony segments in order to adjust the 3D alignment in the frontal plane, sagittal plane and coronal plane (step 32). The surgeon visualizes in real time all required information thanks to the navigation station and modifies, if necessary, the distraction (step 33). The desired 3D alignment is then maintained (step 34). The reaming guide is placed (step 35) and two volumes are reamed in the desired alignment: a first volume of bone on the first bony segment and a second volume of bone on the second bony segments (step 36). The implant size is chosen following the size of the reamed volume and the implant is placed inside the reamed volume (step 37). This implant is finally maintained between both bony segments in order to fix the relative position of both bony segments (step 38). The reaming guide and the trackers can be finally removed (step 39).

The main advantage of the invention is to provide an apparatus and a method allowing the surgeon to adjust and maintain accurately the alignment in the three dimensions (3D) for the placement of a wedge implant for osteotomies.

The invention claimed is:

1. A system of attachment of a first bony segment in relation with a second bony segment, both segments belonging to a same bone, wherein the system comprises:
    two trackers, each tracker being configured for attaching to a respective segment prior to said segments being maintained together by a hinge to be formed by a partial cut of said bone;
    a navigation system adapted to acquire three-dimensional positions and orientations of said trackers;
    a processing system adapted to compute, from the data given by said navigation system, three dimensional alignment angles of the two said segments;
    a display unit adapted to show information to the surgeon;
    reaming guides of different sizes, wherein each reaming guide defines a bone volume to be removed from each segment on both sides of the hinge;
    implants of different sizes, wherein a shape of each implant coincides with a shape of the bone volume defined by a correspondingly sized one of said reaming guides, said implant being configured to be inserted into a global volume comprising the bone volumes removed from each segment and a distraction volume separating said bone volumes;
    two bases, each configured to be attached to a respective segment on both sides of the hinge;
    said reaming guides configured to be fixed to each of both bases over the hinge.

2. The system according to claim 1, wherein each tracker is attached to one of said two bases, each said base for being fixed with at least one pin or screw to each said segment.

3. The system according to claim 2, wherein each base comprises two fixing pins and a receiving support of a corresponding tracker.

4. The system according to claim 1, comprising at least one distractor configured to maintain the desired position between both segments.

5. The system according to claim 4, wherein each tracker is attached to a respective base and said at least one distractor is attached between both bases.

6. The system according to claim 4, wherein said at least one distractor is adjustable in length.

7. The system according to claim 1, wherein at least one of said reaming guides is adjustable optionally in length, so as to be adapted according to distraction of the bone segments.

8. The system according to claim 1, wherein each of said reaming guides has at least one reaming hole with a specific shape.

9. The system according to claim 1, wherein each of said reaming guides comprises at least one fixation system in relation with the bone.

10. The system according to claim 9, wherein each of said reaming guides is attached onto a base.

11. The system according to claim 9, wherein said fixation system permits detaching each of said reaming guides and replacing a detached reaming guide with another one.

12. The system according to claim 9, wherein said fixation system is a locked tenon and mortise joint.

13. The system according to claim 1, wherein at least one implant has the same volume as distraction size and reamed global volume.

14. The system according to claim 1, wherein at least one implant is adjustable following said distraction size.

15. The system according to claim 1, wherein said display unit is directly carried by at least one of said trackers.

16. The system according to claim 1, wherein said trackers are optic or magnetic.

17. The system according to claim 1, wherein said processing system is directly carried by at least one of said trackers.

* * * * *